United States Patent [19]

Rodder

[11] Patent Number: 4,961,344
[45] Date of Patent: Oct. 9, 1990

[54] MULTIPLE TUBE FLOWMETER

[76] Inventor: Jerome A. Rodder, 775 Sunshine Dr., Los Altos, Calif. 94022

[21] Appl. No.: 351,183

[22] Filed: May 12, 1989

[51] Int. Cl.$^5$ .......................... G01F 1/48; G01F 5/00; A01B 5/087

[52] U.S. Cl. .................................. 73/202; 73/861.52; 128/725

[58] Field of Search .................. 73/202, 202.5, 204.27, 73/862.52; 128/724, 725

[56] References Cited

U.S. PATENT DOCUMENTS

| | | | |
|---|---|---|---|
| 2,163,730 | 6/1939 | Goetzl | 73/202 |
| 3,559,482 | 2/1971 | Baker et al. | 73/202.5 |
| 3,838,598 | 10/1974 | Tompkins | 73/861.52 |
| 4,475,387 | 10/1984 | Hawn et al. | 73/202.5 |
| 4,519,246 | 5/1985 | Hartemink | 73/204.27 |
| 4,800,754 | 1/1989 | Korpi | 73/202 |

Primary Examiner—Herbert Goldstein
Attorney, Agent, or Firm—Christie, Parker & Hale

[57] ABSTRACT

A gas flow measuring appartaus especially useful in a spirometer produces increased gas flow sensitivity and accurate gas flow rate measurements, especially at low gas flow rates. The apparatus includes a breath transmission passage, first and second ports spaced apart axially along the passageway, and a gas flow meter connected across the ports for measuring gas flow rate in the passageway. A plurality of elongated small diameter hollow tubes are mounted within the passageway proximate the locations at which the gas flow measuring ports communicate with the passageway. The small diameter tubes act as a restriction within the passageway for causing gas flow entering the passageway to flow past and through the tubes and toward the outer walls of the passageway, thereby producing a pressure drop across the ports that results in measurable gas flow rate measurements at the flowmeter. The small diameter hollow tubes may be mounted in an elongated restriction tube in the passageway proximate the gas flow measuring ports, or the hollow tubes also may be mounted to the inner wall of the passageway, both in arrangements which increase the gas flow rate measuring sensitivity of the flowmeter, while producing substantially negligible resistance to gas flow that produces a laminar and substantially uniform gas flow pattern along the outer walls of the passageway.

27 Claims, 2 Drawing Sheets

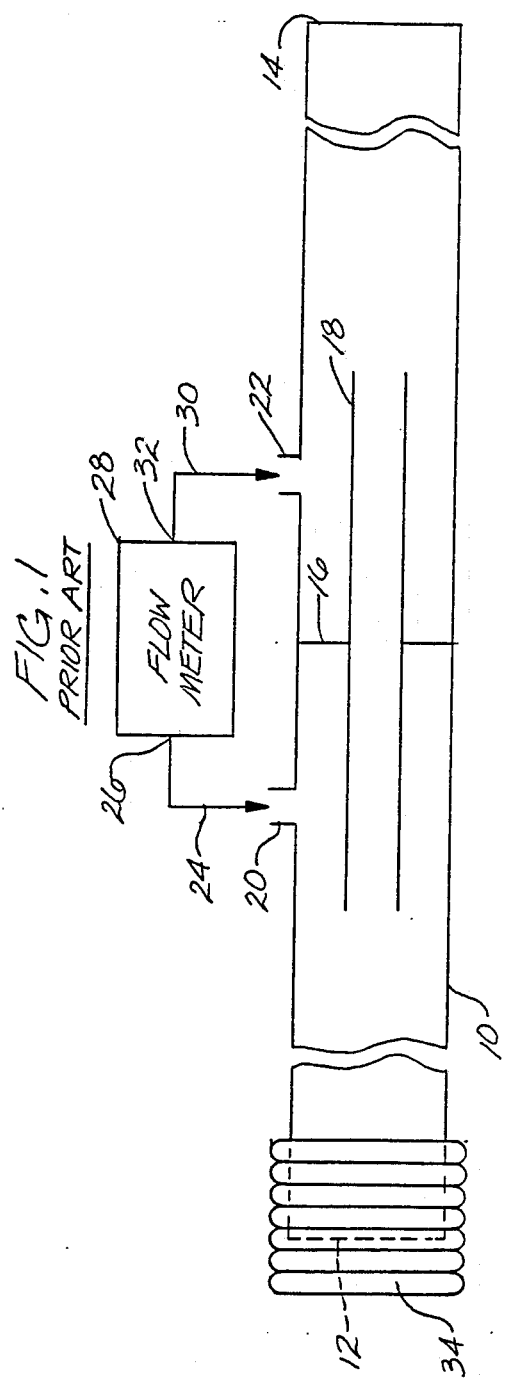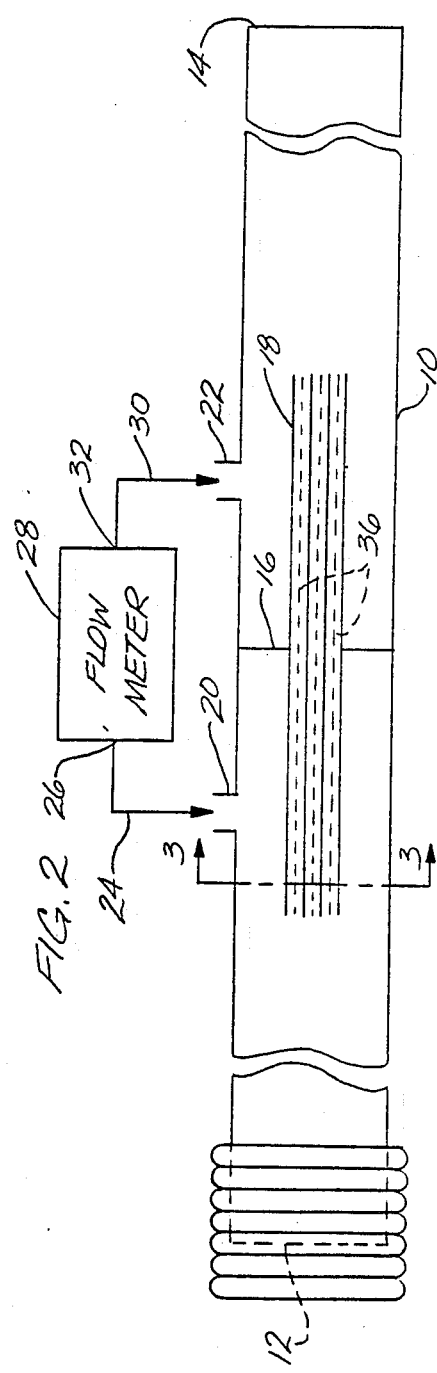

MULTIPLE TUBE FLOWMETER

FIELD OF THE INVENTION

This invention relates to an apparatus for measuring fluid flow and, more particularly, to a multiple tube flowmeter useful in providing accurate measurements of gas flow rate in a spirometer.

BACKGROUND OF THE INVENTION

My U. S. Pat. Nos. 3,735,752; 3,947,739; 4,090,406; 4,163,390; 4,259,968 and my U.S. Pat. Application Serial No. 236,546, filed August 25, 1988, which relate generally to spirometers, flowmeters and related sensitive fluid flow measuring systems are fully incorporated herein by this reference.

My U. S. Pat. Nos. 4,163,390 and 4,259,968 describe a spirometer having a breath transmission passage with opposite ends open to the atmosphere. A restriction inside the passage produces a pressure drop in the passage in response to inhalation or exhalation by a patient into the end of the passage. The restriction is formed by an elongated, small-diameter tube extending along the main axis of the breath transmission passage. A pair of flow measurement passages in the breath transmission passage adjacent the restriction are coupled to a flowmeter which measures the pressure drop near the restriction. This provides a measurement of gas flow rate in the breath transmission passage.

When the breath transmission passage has a large diameter (approximately one inch diameter or more), and when the gas flow rate through the passage is low and the gas flow enters the passage from a corrugated tube attached to the passage, no output signal is developed by the flowmeter because the pressure drop across the flow measurement passages is too low. Use of a largediameter tube for the breath transmission passage of a spirometer is desirable; but when the diameter is large and the gas flow rate is low, the gas tends to flow toward the center of the passage. Therefore, there is no pressure drop near the outside of the passage, including the region connected to the flowmeter. It is a standard practice in the use of spirometers to use a flexible corrugated tube attached to the spirometer breath transmission passage. The flexibility of the corrugated tube is a desirable attribute during use, but gas flow into the breath transmission passage is not laminar for low gas flow rates because the corrugations in the tubing create small eddy currents near the outer wall of the passage, near its connection to the corrugated tubing. The loss of a more laminar and uniform gas flow prevents the necessary pressure drop near the outside of the breath transmission passage and results in inaccurate readings or no signal at all at the flowmeter.

One technique for producing a more laminar flow through the breath transmission passage is to place a screen across the cross section of the passage. However, the screen needs a support, and this creates turbulent flow, especially at higher gas flow rates. Another serious drawback is that the screen can be clogged from the patient's coughing.

The present invention provides a multiple tube fluid flow measuring device useful in a spirometer for producing accurate flowmeter signals for gas flow through a breath transmission passage having a large diameter, when the gas flow rate through the passage is low, and when the gas flow enters the passage from a corrugated tubing. The multiple tube fluid measuring device makes gas flow more laminar through the cross section of the passage and produces a measurable pressure drop near the flow measuring passages leading to the flowmeter, even for low gas flow rates. The low flow rate sensitivity of the measuring device is increased substantially over prior art measuring devices, while producing a negligible increase in gas flow resistance through the breath transmission passage.

SUMMARY OF THE INVENTION

Briefly, one embodiment of the present invention provides gas flow measuring apparatus comprising a passageway having a flow path, a first port in gas communication with the passageway, a second port in gas communication with the passageway at a location spaced apart along the flow path from the location at which the first port communicates with the passageway, means adapted for connection to first and second ports for measuring gas flow rate through the passageway, and a plurality of elongated hollow tubes within the passageway proximate the locations at which the first and second ports communicate with the passageway. The hollow tubes extend generally axially with respect to the passageway for causing gas flow in the passageway to travel through the passageway in a generally uniform, cross-sectional flow pattern to produce a means for generating a pressure drop near the outside of the passageway so that low gas flow through the passageway can be detected across the first and second ports and measured by the gas flow rate measuring means.

In an embodiment in which a restriction formed in the main passageway is produced by a smaller diameter inner tube, the plurality of hollow tubes can be mounted within the smaller diameter inner tube to extend along the axis of the passageway. The hollow tubes tend to produce a more uniform flow pattern through the entire passageway, and this more uniform gas flow tends to be more laminar and is produced near the outside of the passage for being detected and measured by the flowmeter. The result is a gas flow measuring device with excellent low flow sensitivity and accuracy.

These and other aspects of the invention will be more fully understood by referring to the following detailed description and the accompanying drawings.

BRIEF DESCRIPTION OF THE DRAWINGS

FIG. 1 is a schematic diagram illustrating a prior art gas flow rate measuring device.

FIG. 2 is a schematic diagram illustrating a gas flow measuring device according to the principles of this invention.

DETAILED DESCRIPTION

Figure 3:
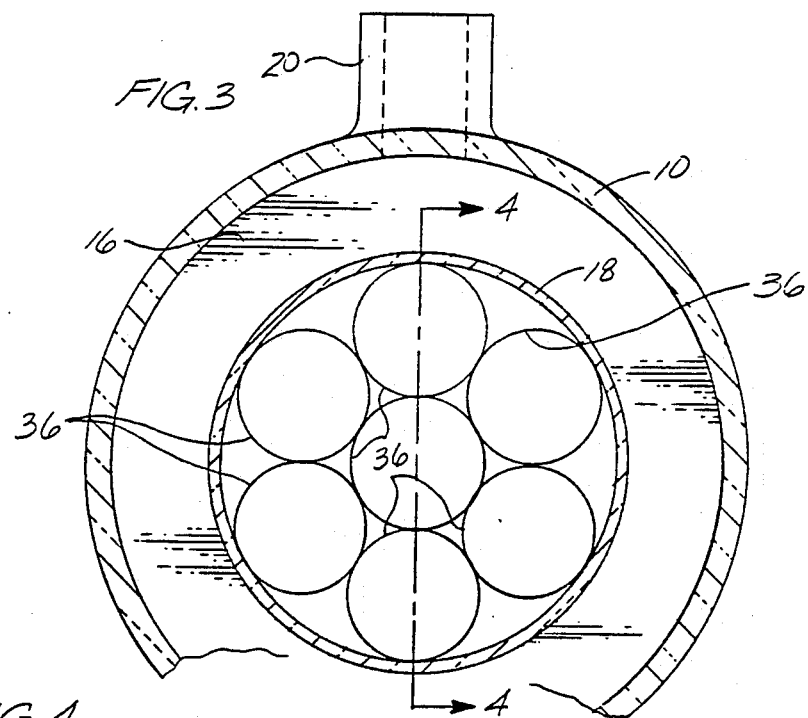
FIG. 3 is a schematic, cross-sectional view taken on line 3—3 of FIG. 2.
Figure 4:
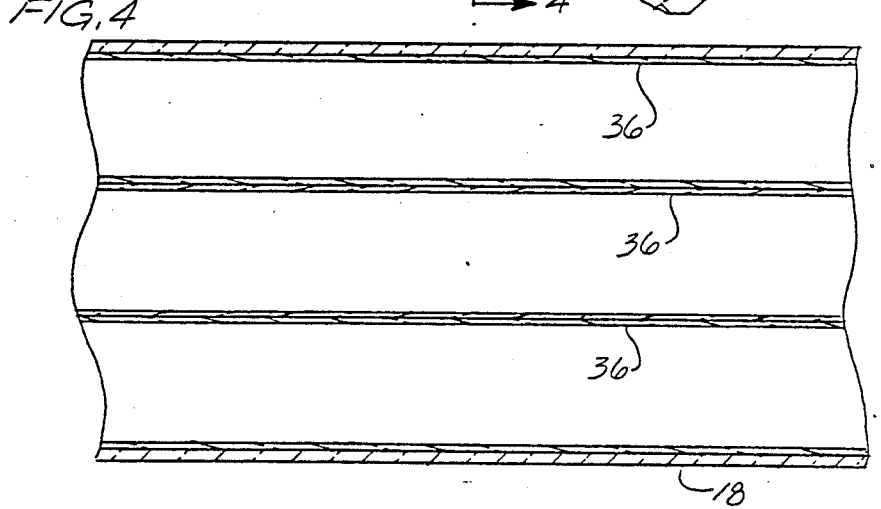
FIG. 4 is a fragmentary schematic, cross-sectional view taken on line 4—4 of FIG. 3.

FIG. 1 shows an elongated large-diameter tubular breath transmission passage 10 having opposite ends 12 and 14 open to the atmosphere. Midway between the ends 12 and 14 of the breath transmission passage 10, an annular partition 16 extends perpendicularly across the outer portion of the breath transmission passage. An elongated restriction tube 18 having a smaller diameter than the breath transmission passage extends centrally along the axis of the breath transmission passage. The restriction tube passes through the partition to provide fluid communication between the ends 12 and 14 of the breath transmission passage. The restriction tube serves as a restriction on air flowing between the ends of the breath transmission passage and is a means for producing sufficient gas pressure drop along its length, adjacent the outer wall of the passage 10, for use in measuring gas flow rate through the passage.

The breath transmission passage 10 has a first intermediate port 20 between the ends 12 of the passage and the partition 16 and a second intermediate port 22 between the end 14 of the passage 10 and the partition 16. The intermediate ports 20 and 22 also are referred to herein as breath flow rate measuring ports or passages. The first intermediate port 20 is connected by flexible tubing 24 to a port 26 of a pressure comparator or gas flow meter shown generally at 28. The second intermediate port 22 is connected by flexible tubing 30 to a port 32 of the pressure comparator or flowmeter 28. Preferably, the intermediate ports 20 and 22 are located near the restriction, i.e., between the ends of the smaller diameter restriction tube, where the gas velocity is low and turbulence inside the passage is small. The breath transmission passage has a suitable cross-sectional area for lung capacity of the particular patient using the device.

During use, when a patient exhales into the end 12 of the breath transmission passage 20, there is a pressure drop from the end 12 to the end 14 by virtue of the restriction provided by the tube 18. Therefore, the pressure at port 26 of the flowmeter rises, and the pressure at the port 32 drops. Thus, there will be gas flow through the flowmeter from port 26 to port 32.

When the patient inhales from the end 12 of the breath transmission passage 10, there is a pressure drop from the port 32 to the port 26 of the flowmeter by virtue of the restriction provided by the inner tube 18. Thus, as the pressure at the port 32 rises, and the pressure at the port 26 drops, the pressure difference results in gas flow through the flowmeter from port 32 to port 26.

Gas flow through the flowmeter is proportional to the pressure difference in the tubings leading to the ports of the flowmeter, and this pressure difference is directly proportional to the flow rate of breathing gas through the breath transmission passage 10.

As described previously, when the inside diameter of the breath transmission passage 10 is large, say approximately one inch in diameter or greater, and the gas flow rate through the passage is low, and the gas flow enters the passage from a corrugated tube such as the tubing 34 connected to the end 12 of the passage, no signal is generated by the flowmeter because the pressure drop across the ports 20 and 22 is too low. The gas flow entering the passage also is not laminar because the corrugated tubing 34 creates small eddy currents which prevent the necessary pressure drop from developing downstream adjacent the ports 20 and 22.

FIG. 2 schematically illustrates one form of the present invention in which a number of elongated smaller diameter thin-walled hollow metal tubes 36 are mounted inside the restriction tube 18. The smaller diameter metal tubes 36 each extend approximately the same length the restriction tube 18, i.e., beyond opposite sides of the regions where the intermediate ports 20 and 22 open into the breath transmission passage 10. The smaller diameter tubes 18 extend axially along the inside diameter of the restriction tube. They are preferably of circular cross section, of the same or similar inside diameter, and of uniform diameter from end to end. They are mounted so that their respective axes are parallel to the main axis of the restriction tube 18 and the breath transmission passage 10. The smaller diameter tubes 36 also are rigidly mounted in the I. D. of the restriction tube 18, preferably by cementing them in place so they are held in a fixed position during use. In a preferred form of the invention, the smaller diameter tubes collectively fill the cross section of the restriction tube 18. That is, the tubes 36 are not left with spaces between them. The O. D. of the tubes is machined precisely so the tubes fit within the restriction tube by all contacting one another and also by contacting the I.D. of the restriction tube.

During use, the smaller diameter tubes 36 produce greatly improved low gas flow rate sensitivity and resulting accurate readings of gas flow rate at the flowmeter. Gas flow entering the passageway from either end flows toward the hollow metal tubes 36, and past the tubes, as well as through the tubes. The tubes 36 cause this gas flow, especially at low flow rates (which would otherwise flow toward the center of the breath transmission passage as in the embodiment of FIG. 1), to flow toward and along the outer side walls of the passage 10. This gas flow, which has been diverted along the outside walls of the passage, produces a measurable pressure drop at the intermediate ports 20 and 22, in the areas where pressure drop is needed to produce readings at the flowmeter. The thin-walled tubes also produce negligible flow resistance and thereby cause the gas flow along the outer walls of the breath transmission passage to flow in a laminar flow pattern. As a result, the gas flow through the tube has a more uniform pressure drop in planes perpendicular to the main axis of the breath transmission passage.

The result is increased sensitivity in measuring gas flow rate at the flowmeter and increased accuracy by the absence of flow resistance and the resulting laminar flow pattern and uniform pressure drop of the flow through the tube. The thin-walled metal tubes 36 produce such increased sensitivity and accuracy even in situations where the gas flow rate entering the tube is low and the gas enters the tube from a corrugated tubing attached to the front end of the tube.

In one embodiment, the restriction tube 18 has a diameter of about one-half to three-fourths inch, and thin-walled metal tubes 36 with a diameter of about one-fourth inch to about one-third inch are cemented in place in the tube 18, say in a manner similar to the arrangement shown in FIG. 3. In this embodiment, sensitivity is increased by a factor of about ten, with a negligible increase in gas flow resistance.

This arrangement has advantages over use of a porous screen in the breath transmission passage because the thin-walled metal tubes are much larger in diameter than the pores of the screens and particulates do not clog the restriction. In addition, turbulent gas flow (especially at high gas flow rates) produced by the screen are avoided by the thin-walled metal tubes.

Figure 5:
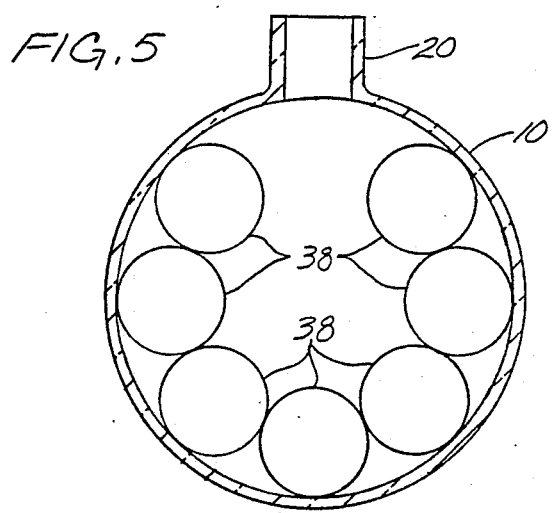
FIG. 5 is a schematic, cross-sectional view illustrating an alternative form of the invention.

FIG. 5 shows an alternate embodiment of the invention in which the thin-walled smaller diameter metal tubes are cemented in place around the inner wall of the breath transmission passage 10. In this embodiment, the tubes 38 extend for the same length as the tubes shown in the embodiment of FIG. 2. This embodiment also can produce increased sensitivity with negligible flow resistance to gas flow, especially at low gas flow rates. This embodiment can also be used in combination with a restriction tube such as the tube 18 illustrated in FIG. 2.

Other embodiments are also possible for arranging thin-walled, smaller diameter tubes in a breath transmission passage at locations within the passage which communicate with pressure drop sensing means, so that gas flow which would normally pass through the center of the tube, especially at low gas flow rates, is diverted more toward the outer wall of the passage, and flows in a reasonably laminar and uniform flow pattern, so that gas flow rate sensitivity and gas flow rate measuring accuracy are improved.

What is claimed is:

1. A gas flow measuring apparatus comprising:
   a passageway having a flow path;
   a first conduit in communication with the passageway;
   a second conduit in communication with the passageway at a location spaced apart along the flow path from the location at which the first conduit communicates with the passageway;
   an elongated hollow restriction tube within the passageway spaced inwardly from the passageway and extending substantially parallel to the axis of the passageway and extending in opposite directions beyond the locations at which the first and second conduits communicate with the passageway;
   gas flow measuring means connected to the first and second conduits for measuring the flow rate of gas through the passageway; and
   a plurality of elongated, smaller diameter hollow tubes within the hollow restriction tube, the smaller diameter tubes having axes of elongation substantially parallel to the axis of the restriction tube, for causing gas flow entering the passageway to flow past and through the smaller diameter tubes in the restriction tube, while producing substantially negligible resistance to gas flow therethrough to cause gas flow along the walls of the passageway to thereby produce a pressure drop at the first and second conduits sufficient for producing a measurable reading at the gas flow measuring means.

2. Apparatus according to claim 1 wherein the tubes extend between the locations at which the conduits communicate with the passageway.

3. Apparatus according to claim 2 wherein the tubes also extend in opposite directions beyond the locations at which the conduits communicate with the passageway.

4. Apparatus according the claim 1 in which the smaller diameter tubes are of similar diameter, are substantially circular in cross section, and are of substantially uniform diameter from end to end.

5. Apparatus according to claim 1 in which the smaller diameter tubes substantially fill the cross section of the restriction tube by collectively connecting the inside wall of the restriction tube and contacting the outer walls of one another.

6. Apparatus according to claim 1 in which the restriction tube and the smaller diameter tubes therein divert gas flowing at low gas flow rates to produce a substantially laminar and uniform gas flow pattern along the walls of the passageway in the annulus between the restriction tube and the passageway to produce said measurable readings of gas flow rate.

7. Apparatus according to claim 6 in which the smaller diameter tubes are confined to the interior of the restriction tube and substantially absent from the annulus between the restriction tube and the wall of the passageway.

8. Apparatus according to claim 1 in which the smaller diameter tubes are thin-walled, smooth surfaced uniform diameter tubes.

9. Apparatus according to claim 1 in which the passageway has a diameter greater than about one inch, the restriction tube has a diameter greater than about one-half inch, and the smaller diameter tubes have a diameter from about one-third to about one-fourth inch.

10. A spirometer apparatus for measuring gas flow from a patient exhaling or inhaling through a tube, the apparatus comprising:
    a flow tube elongated along an axis and having an interior flow path along the axis, the flow tube comprising a breath transmission tube with sufficient cross-sectional area for measuring breath flow rate of a patient exhaling or inhaling through the flow tube;
    a first port in gas communication with the flow tube;
    a second port in gas communication with the flow tube spaced apart from the first port with respect to the flow tube axis;
    an elongated hollow restriction tube within the flow tube spaced inwardly from the flow tube and extending substantially parallel to the axis of the flow tube and extending in opposite directions beyond the locations at which the first and second ports communicate with the flow tube;
    gas flow measuring means connected to the first and second ports for measuring the flow rate of gas flow from a patient exhaling or inhaling through the flow tube; and
    a plurality of elongated, smaller diameter hollow tubes within the hollow restriction tube and having axes of elongation substantially parallel to the axis of the restriction tube for causing gas flow entering the flow tube to flow past and through the smaller diameter tubes in the restriction tube while producing substantially negligible resistance to gas flow therethrough to cause gas flow along the walls of the flow tube and thereby produce a corresponding pressure drop across the first and second ports to produce measurable readings of exhalation and inhalation gas flow in the flow tube at the gas flow measuring means.

11. Apparatus according to claim 10 wherein the tubes extend between the locations at which the conduits communicate with the passageway.

12. Apparatus according to claim 11 wherein the tubes also extend in opposite directions beyond the locations at which the conduits communicate with the passageway.

13. Apparatus according to claim 10 in which the smaller diameter tubes are of similar diameter, are substantially circular in cross section, and are of substantially uniform diameter from end to end.

14. Apparatus according to claim 10 in which the smaller diameter tubes substantially fill the cross section of the restriction tube by collectively contacting the inside wall of the restriction tube and contacting the outer walls of one another.

15. Apparatus according to claim 10 in which the restriction tube and the smaller diameter tubes therein divert gas flowing at low gas flow rates to produce a substantially laminar and uniform gas flow pattern along the walls of the flow tube in the annulus between the restriction tube and the passageway to produce said measurable readings of gas flow rate.

16. Apparatus according to claim 10 in which the smaller diameter tubes are confined to the interior of the restriction tube and substantially absent from the annulus between the restriction tube and the wall of the flow tube.

17. Apparatus according to claim 10 in which the smaller diameter tubes are thin-walled, smooth surfaced uniform diameter tubes.

18. Gas flow measuring apparatus comprising:
an elongated passageway having an axial flow path;
first and second gas flow measuring means spaced apart along the axis of the passageway and in gas communication with the passageway to provide a means for measuring gas flow rate in the passageway in response to a pressure drop existing between the first and second gas flow measuring means;
an elongated hollow restriction tube within the passageway spaced inwardly from the passageway and extending substantially parallel to the axis of the passageway between the first and second gas flow measuring means;
a plurality of elongated, smaller diameter hollow tubes mounted within the hollow restriction tube, the smaller diameter tubes having axes of elongation substantially parallel to the axis of the restriction tube, said smaller diameter hollow tubes extending axially and being positioned within the restriction tube and the restriction tube being positioned within the passageway for causing gas flow entering the passageway to flow in a laminar flow pattern along the walls of the passageway and past and through the hollow tubes in the restriction tube so that a resulting gas pressure drop can be detected across the first and second gas flow measuring means so that gas flowing in the passageway at low gas flow rates which are substantially not measurable without the presence of the smaller diameter tubes in the restriction tube produces said gas pressure drop at a sufficient magnitude to produce a measurable gas flow rate detected across the first and second gas flow measuring means.

19. Apparatus according to claim 11 in which the restriction tube, and the plurality of tubes, extends in opposite directions beyond the locations at which the gas flow measuring means are in communication with the flow path.

20. Apparatus according to claim 19 in which the passageway has a diameter greater than about one inch, the restriction tube has a diameter greater than about one-half inch, and the smaller diameter tubes have a diameter from about one-third to about one-fourth inch.

21. Apparatus according to claim 18 in which the passageway has a diameter greater than about one inch, the restriction tube has a diameter greater than about one-half inch, and the smaller diameter tubes have a diameter from about one-third to about one-fourth inch.

22. Apparatus according to claim 18 in which the smaller diameter tubes are of similar diameter, are substantially circular in cross section, and are of substantially uniform diameter from end to end.

23. Apparatus according to claim 18 in which the smaller diameter tubes substantially fill the cross section of the restriction tube by collectively contacting the inside wall of the restriction tube and contacting the outer walls of one another.

24. Apparatus according to claim 18 in which the restriction tube and the smaller diameter tubes therein divert gas flowing at low gas flow rates to produce a substantially laminar and uniform gas flow pattern along the walls of the passageway in the annulus between the restriction tube and the passageway to produce said measurable readings of gas flow rate.

25. Apparatus according to claim 18 in which the smaller diameter tubes are confined to the interior of the restriction tube and substantially absent from the annulus between the restriction tube and the wall of the passageway.

26. Apparatus according to claim 18 in which the smaller diameter tubes are thin-walled, smooth surfaced uniform diameter tubes.

27. A method for measuring breath flow rate of a patient exhaling or inhaling through a gas flow tube in a spirometer apparatus which includes a flow tube elongated along an axis and having an interior flow path along the axis, a first port in gas communication with the flow tube, a second port in gas communication with the flow tube spaced apart from the first port with respect to the flow tube axis, an elongated hollow restriction tube within the flow tube spaced inwardly from the flow tube and extending substantially parallel to the axis of the flow tube and positioned within the flow tube so that a gas flow measuring means connected to the first and second ports can measure the flow rate of gas flow in the flow tube produced by the patient exhaling or inhaling through the flow tube, the method comprising positioning a plurality of elongated, smaller diameter hollow tubes within the hollow restriction tube, the hollow diameter tubes having axes of elongation substantially parallel to the axis of the restriction tube; causing gas flow entering the flow tube to flow past and through the smaller diameter tubes contained within the restriction tube while producing substantially negligible resistance to gas flow therethrough to thereby cause gas flow along the walls of the flow tube to produce a pressure drop at the first and second ports of the flow tube; and detecting a measurable reading at the gas flow measuring means for low gas flow rates of said gas flow entering the flow tube, wherein gas flow rates which would otherwise not produce a measurable gas flow rate in the absence of the smaller diameter tubes contained within the restriction tube are detected b the gas flow measuring means.

* * * * *

UNITED STATES PATENT AND TRADEMARK OFFICE
CERTIFICATE OF CORRECTION

PATENT NO.  : 4,961,344

DATED       : October 9, 1990

INVENTOR(S) : Jerome A. Rodder

It is certified that error appears in the above-identified patent and that said Letters Patent is hereby corrected as shown below:

Column 1, line 37, change "largediameter" to
          -- large-diameter --.

Column 3, line 66, after "length" and before "the" insert
          -- as --.

Column 5, line 59, change "connecting" to -- contacting --.

Column 8, line 57, change "b" to -- by --.

Signed and Sealed this

Twenty-first Day of April, 1992

Attest:

HARRY F. MANBECK, JR.

*Attesting Officer*     *Commissioner of Patents and Trademarks*